United States Patent [19]

Kitajima

[11] Patent Number: 5,300,965
[45] Date of Patent: Apr. 5, 1994

[54] CORNEAL SHAPE MEASURING APPARATUS

[75] Inventor: Nobuaki Kitajima, Tokyo, Japan

[73] Assignee: Kabushiki Kaisha Topcon, Tokyo, Japan

[21] Appl. No.: 876,799

[22] Filed: May 1, 1992

[30] Foreign Application Priority Data

May 2, 1991 [JP] Japan .................................. 3-100761

[51] Int. Cl.$^5$ ............................................. A61B 3/10
[52] U.S. Cl. .................................... 351/212; 351/211; 351/216; 351/217; 351/220
[58] Field of Search ............... 351/210, 211, 212, 216, 351/217, 218, 220, 221, 247

[56] References Cited

U.S. PATENT DOCUMENTS

| | | | |
|---|---|---|---|
| 4,256,385 | 3/1981 | Cohen et al. | 351/212 |
| 4,426,141 | 1/1984 | Holcomb | 351/212 |
| 4,569,576 | 2/1986 | Karpov et al. | 351/212 |
| 4,597,648 | 7/1986 | Feldon et al. | 351/221 |
| 4,685,140 | 8/1987 | Mount, II | 351/212 |
| 4,710,003 | 12/1987 | Masuda et al. | 351/211 |
| 4,772,115 | 9/1988 | Gersten et al. | 351/212 |
| 4,779,973 | 10/1988 | Miller et al. | 351/212 |
| 4,863,260 | 9/1989 | Gersten et al. | 351/221 |
| 5,110,200 | 5/1992 | Snook | 351/212 |

Primary Examiner—Bruce Y. Arnold
Assistant Examiner—Michael A. Papalas
Attorney, Agent, or Firm—Finnegan, Henderson, Farabow, Garrett & Dunner

[57] ABSTRACT

This invention provides a corneal shape measuring apparatus that can correctly measure the shape of the cornea of a subject's eye from an image of a target reflected by the cornea even if the optic axis of a hand-held indicator is inclined with respect to the optic axis of the measuring system when measurements are made. A computing control circuit computes the inclination with respect to the measuring optic axis of an indicator plate from the shape of a guide hole in the indicator plate which had previously been input and the shape of the image of the guide hole, and corrects the image of the indicator reflected by the cornea of the subject's eye based on this inclination.

9 Claims, 7 Drawing Sheets

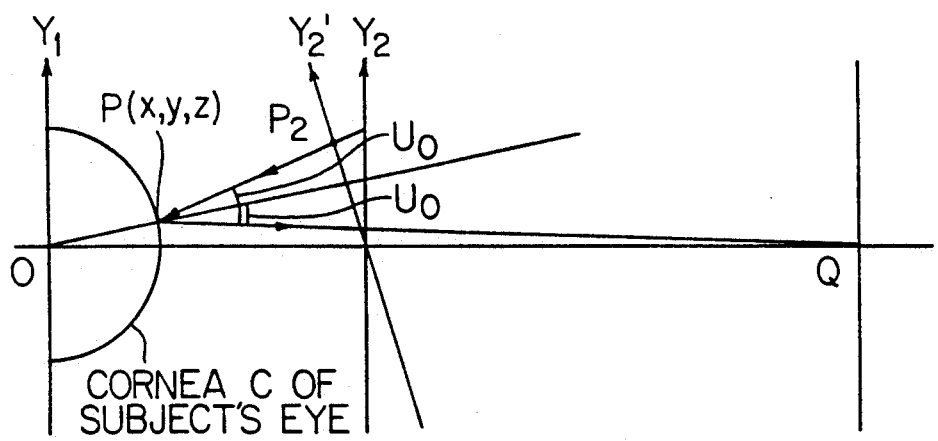
FIG. 7(a)
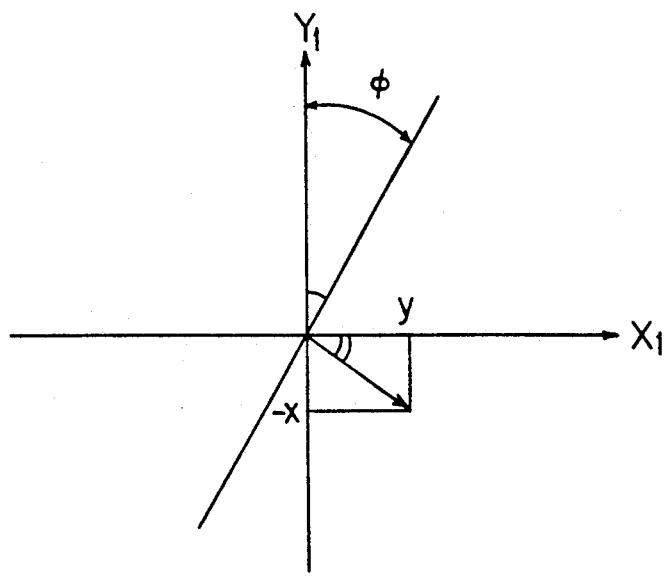
FIG. 7(b)
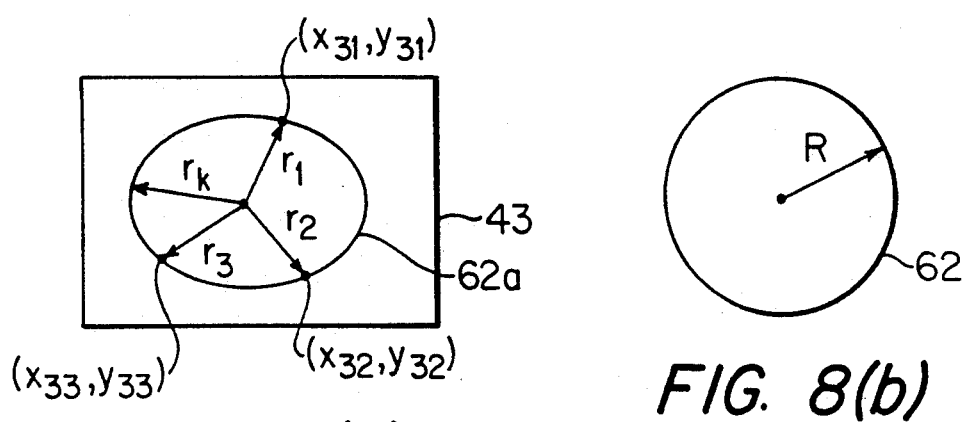
FIG. 8(a)
FIG. 8(b)

CORNEAL SHAPE MEASURING APPARATUS

BACKGROUND OF THE INVENTION

1. Field of the Invention

This invention relates to a corneal shape measuring apparatus which may be used to measure, for example, the shape of the cornea of a subject's eye before and after eye surgery.

2. Description of the Prior Art

In the prior art, it has been the practice to measure the shape of a subject's eye during eye surgery, and in particular during cataract operations. This measurement may be either qualitative or quantitative.

In the qualitative measurement, as shown for example in FIG. 11, an operator 1 places an indicator 2 between the objective lens (not shown) of a surgical microscope 3 and the eye 5 of a subject 4. An image of the indicator 2 is projected onto the cornea of the subject's eye 5 by illuminating light, and the extent of corneal deformation is qualitatively determined by observing the deformation of the image of the indicator 2 reflected by the cornea using the surgical microscope 3.

Alternatively in the quantitative measurement, as shown for example in FIG. 12, an indicator 6 is installed beneath a supporting member 3a of a surgical microscope 3 such that it can be freely inserted or withdrawn from beneath the objective lens (not shown) of the microscope 3, an image of the indicator 6 is projected onto the cornea of a subject's eye 5 by illuminating light. The image of the indicator 6 reflected by the cornea is detected by a photodetector (not shown), and the extent of corneal deformation is quantitatively determined by a computing circuit based on a signal received from this photodetector.

In the aforesaid qualitative corneal shape measuring device, as the operator 1 has to hold the indicator 2 with his hands, it is difficult to position the center axis of the indicator 2 to coincide with the optic axis 0 of the objective lens of the surgical microscope 3.

Further, if the center axis of this indicator 2 is inclined at an angle with respect to the optic axis 0 of the objective lens, the image of the indicator is projected onto the subject's eye at an angle so that the cornea of the eye may appear to be deformed even if it is not.

In the aforesaid quantitative corneal shape measuring apparatus, although the optic axis of the indicator 6 is not inclined with respect to the optic axis 0 of the objective lens as it is in the qualitative method, the indicator 6 is permanently installed underneath and close to the surgical microscope 3. There is, therefore, little space to perform the operation, and the indicator becomes a hindrance when carrying out surgical procedures.

In some cases, it may be required to perform corneal measurements not only close to the optic axis, but also up to the periphery of the subject's eye 5. It is then necessary to move the indicator 6 closer to the cornea to enlarge the projected image of the indicator.

In such a case, however, a mechanism is necessary to move the indicator 6 forward or backward along the optic axis. This is undesirable from a hygiene viewpoint and also makes the apparatus more complex.

SUMMARY OF THE INVENTION

It is, therefore, an object of this invention to provide a corneal shape measuring apparatus wherein an accurate shape measurement of the cornea of a subject's eye can be obtained from the reflected image of a hand-held indicator even if the optic axis of the indicator is inclined with respect to the optic axis of the measuring optical system during the measurement.

To achieve the aforesaid object, the corneal shape measuring apparatus of this invention comprises an illuminating optical system for illuminating the cornea of a subject's eye, a measuring optical system having an objective lens on which reflected light from the cornea of the subject's eye illuminated by the illuminating system impinges, an indicator having a visual target which is projected onto the cornea by the illuminating light, a light guide hole for guiding the image of the target reflected by the cornea to the objective lens and reflecting surfaces aligned with the guide hole so that the illuminating light is reflected, this indicator being disposed between the objective lens and the subject's eye, a photodetector on which the reflected target image and the guide hole image from the reflecting surfaces are projected, a computing circuit which calculates the shape of the reflected target image based on a corresponding signal from the photodetector, computes the inclination of the indicator with respect to the measurement axis from the shape of the guide hole which has previously been input and the shape of the guide hole image, and corrects the shape of the reflected target image accordingly based on the computed inclination so as to determine the actual deformation of the cornea of the subject's eye, and display means which displays the shape of the subject's eye obtained by the computing means.

These and other objects, features and advantages of the present invention will be well appreciated upon reading the following description of the invention in conjunction with the attached drawings with the understanding that some modifications, variations and changes of same could be made by a person skilled in the art to which the invention pertains without departing from the spirit of the invention or the scope of the claims appended hereto.

BRIEF DESCRIPTION OF THE ATTACHED DRAWINGS

FIG. 7(a) and 7(b) are schematic drawings used to describe the correction of the shape of a corneal image.

FIG. 8(a) is a plan view of the reflected target image on the photodetector, and FIG. 8(b) is a schematic drawing showing the shape of the target.

Figure 9:
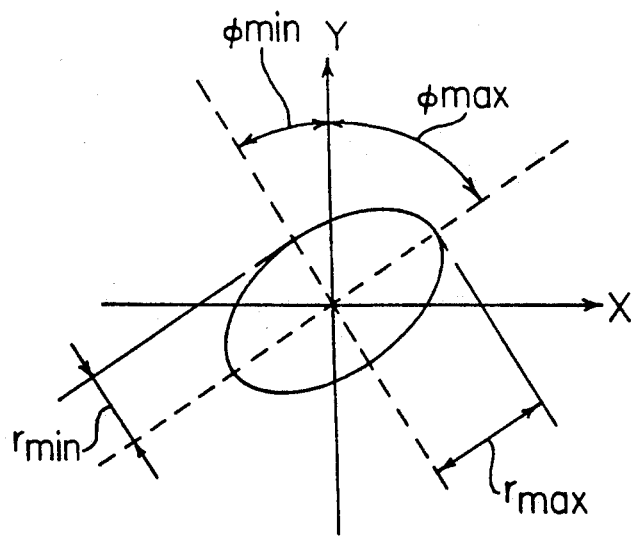

FIG. 9 is a schematic drawing used to describe the correction of the shape of a corneal image.

Figure 10:
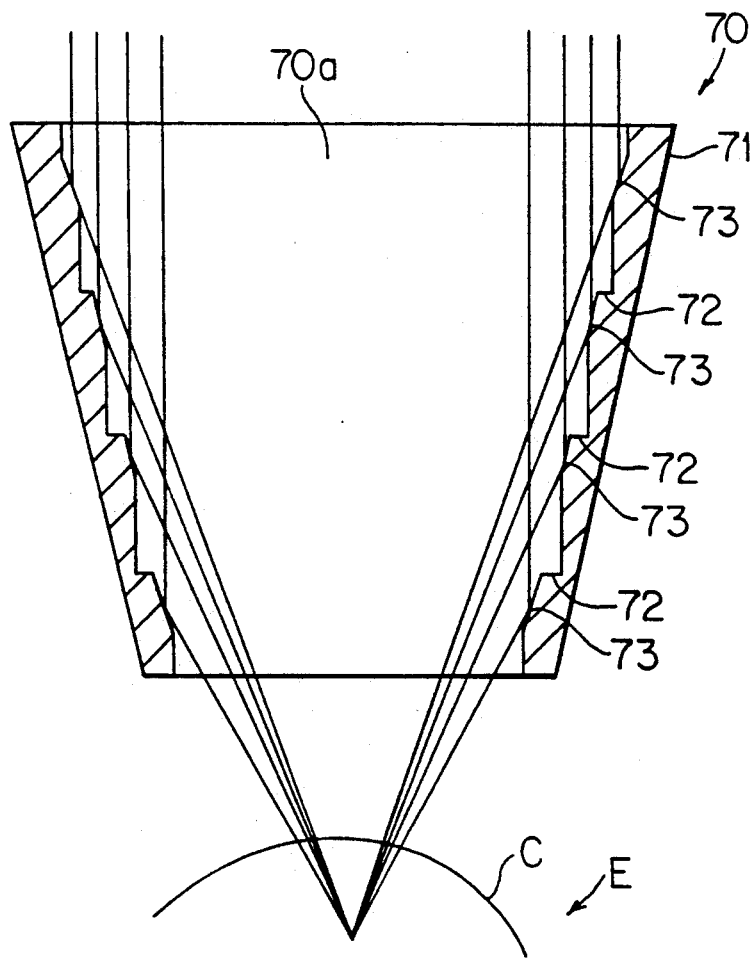

FIG. 10 is a sectional view showing another example of an indicator according to this invention.

Figure 11:
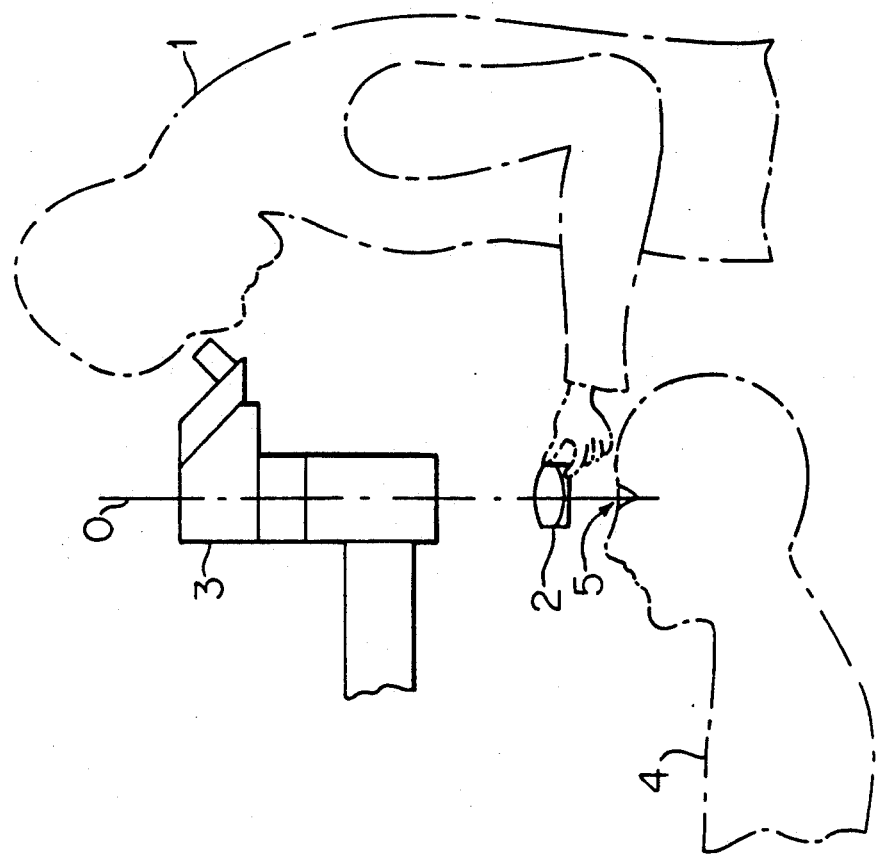

FIG. 11 is a descriptive drawing showing one example of a conventional surgical microscope.

Figure 12:
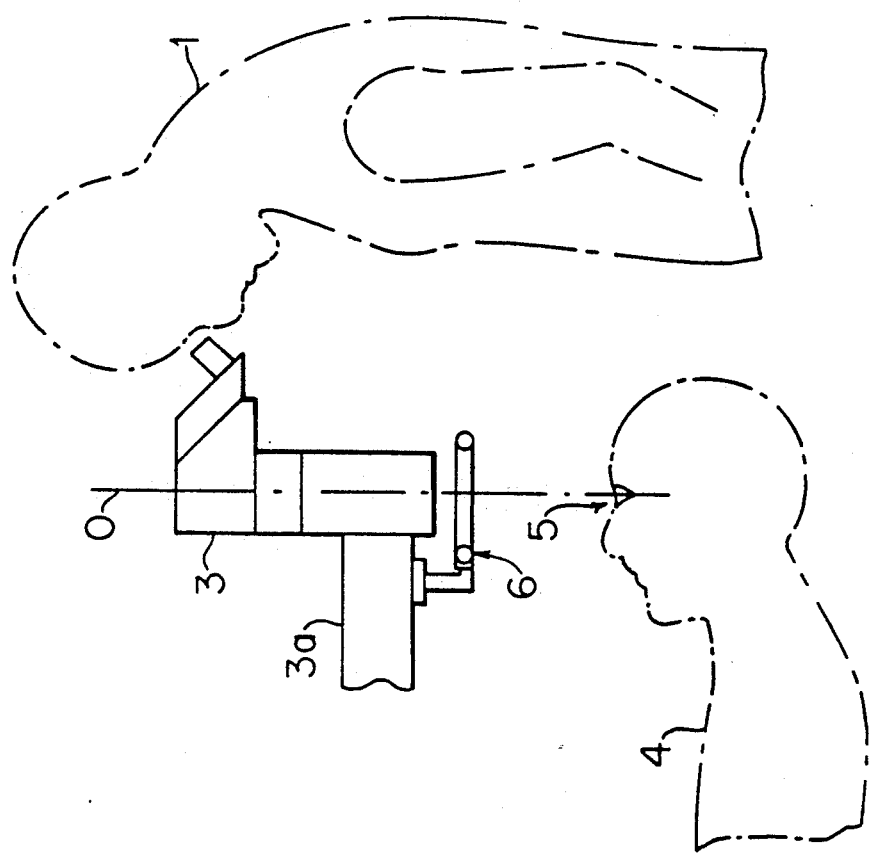

FIG. 12 is a descriptive drawing showing another example of a conventional surgical microscope.

DESCRIPTION OF THE PREFERRED EMBODIMENT

One embodiment of the invention will now be described with reference to FIGS. 1 to 9.

Figure 1:
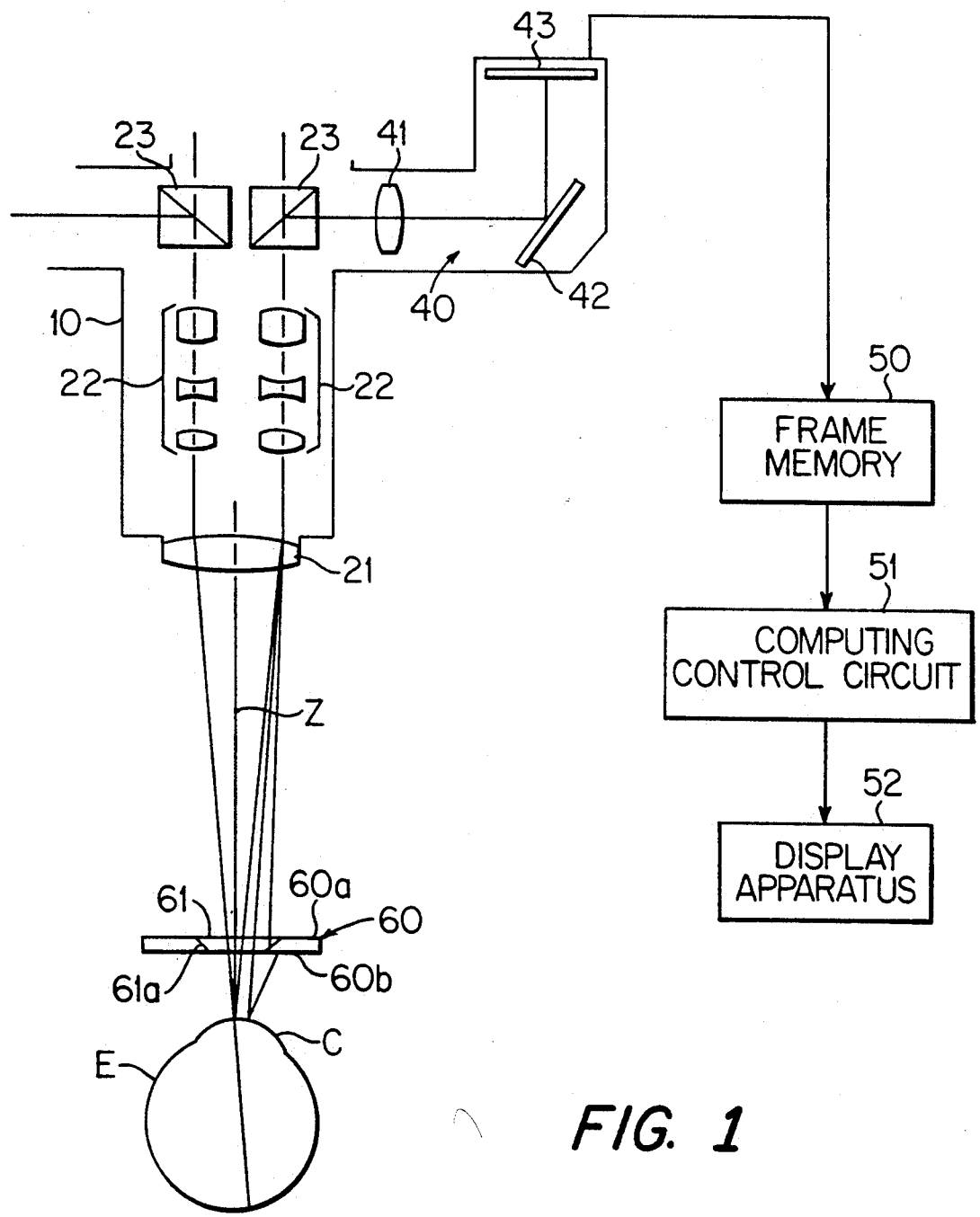
FIG. 1 is a sectional view taken along the line A—A of FIG. 2.
Figure 2:
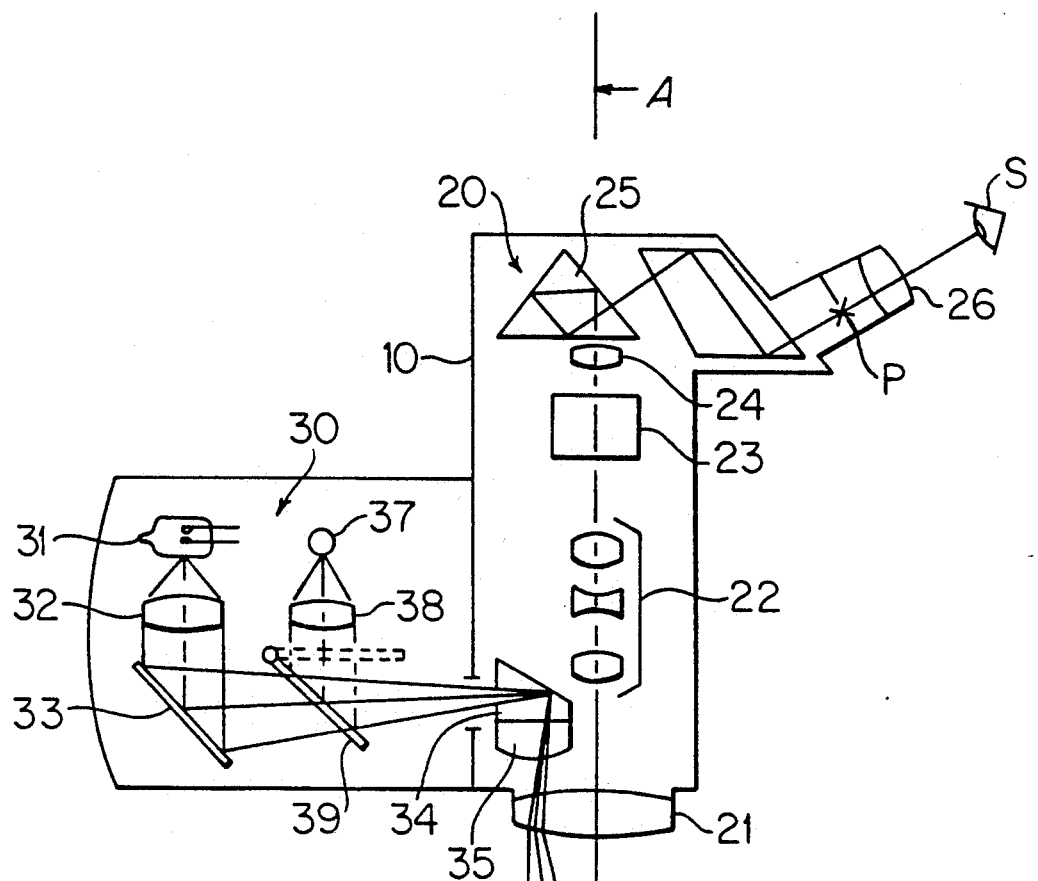
FIG. 2 is a schematic drawing of a corneal shape measuring apparatus according to this invention.

FIGS. 1 and 2 illustrate the construction of a visual light microscope used in surgical operations.

In FIGS. 1 and 2, 10 is a microscope body. The microscope body 10 house an observing optical system 20, an illuminating optical system 30 and a measuring optical system 40.

The observing optical system 20 includes an objective lens 21, variable power lenses 22, beam splitters 23, imaging lens 24, erect prism 25 and eyepiece lens 26 as shown in FIG. 2. In FIG. 1, E is a subject's eye, and in FIG. 2, P is a conjugate point to the cornea C of the subject's eye.

An illuminating optical system 30 includes a halogen lamp 31 as an illuminating source for making observations, condensing lens 32, reflecting mirror 33, prism 34, lens 35 and objective lens 21. The illuminating optical system 30 also includes a xenon lamp 37 as an optical source for making measurements, condensing lens 38, and quick return mirror 39 which can be freely inserted in or withdrawn from the optical path of the observation system.

The measuring optical system 40 includes the objective lens 21, variable power lenses 22, beam splitters 23, imaging lens 41 and reflecting mirror 42. A reflected image of the target from the subject's eye E guided by this measuring optical system 40 is brought to a photodetector 43.

The output signal from the photodetector 43 is input to a frame memory 50 and a computing control circuit 51 (computing means) which determines the shape of the cornea, and a display apparatus 52 displays the shape of the cornea of the subject's eye obtained by the computing control circuit 51. This display apparatus 52 may be a TV monitor, liquid crystal display, etc. A memory, not shown, is connected to the computing control circuit 51 which stores necessary information.

Figure 3A:
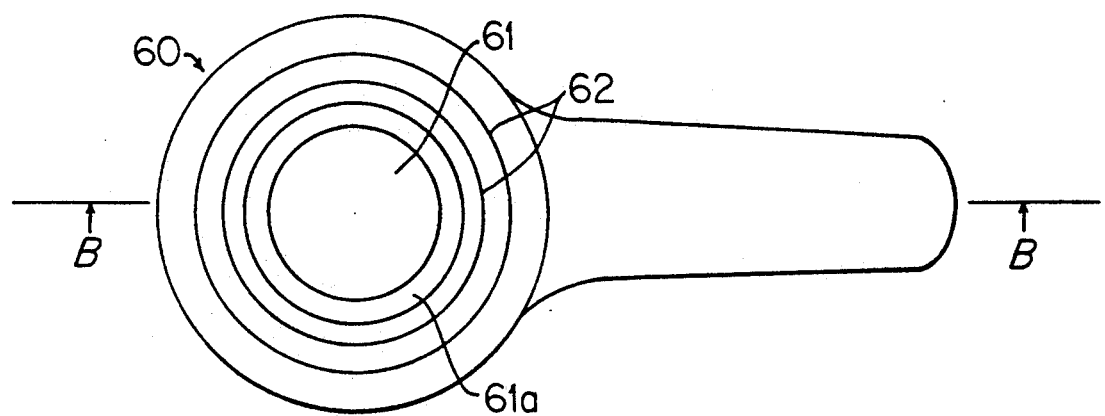
FIG. 3(a) is a plan view of an indicator plate shown in FIG. 1.
Figure 3B:
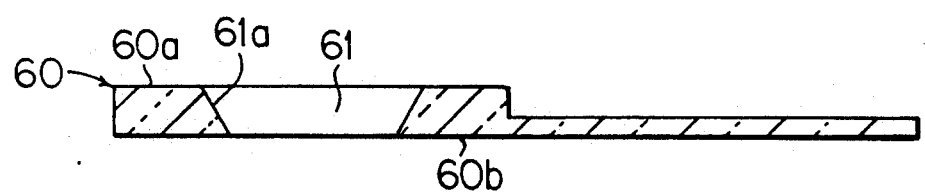
FIG. 3(b) is a sectional view taken along the line B—B of FIG. 3(a).

A hand-held, transparent indicator plate 60 (indicator) is positioned by the operator between the measuring optical system 40 and the subject's eye E. A light guide hole 61 is provided in the center of this plate 60 as shown in FIGS. 1 to 3, and a target 62 (ring pattern) shown in FIG. 3(a) concentric with the guide hole 61 is provided underneath the indicator plate 60 on an indicator surface 60b as shown in FIG. 3(b). Tapered surfaces 61a which widen towards their upper end are formed in this guide hole 61.

Figure 4:
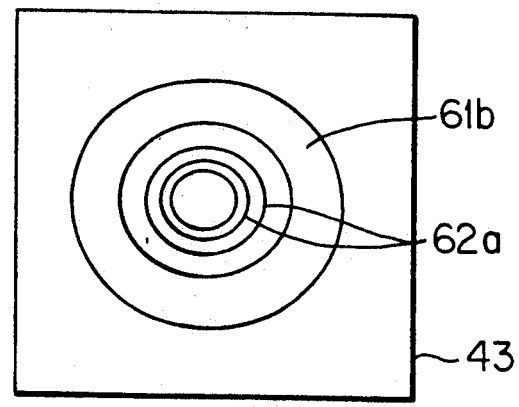
FIG. 4 is a schematic drawing of a reflected target image detected by a photodetector.

The upper surface 60a and the tapered surfaces 61a of the indicator plate 60 form scattering and reflecting surfaces with fine imperfections which directly reflect part of the illuminating light from the illuminating optical system 30. An image 61b of the guide hole is projected by light reflected directly from the tapered surfaces 61a (reflecting surfaces) onto the photodetector 43 as shown in FIG. 4. An image 62a of the target reflected by the cornea C of the subject's eye E is also projected onto the photodetector 43 through the measuring optical system 40.

The computing control circuit 51 is set to compute the inclination with respect to the measurement optic axis of the indicator plate 60 from the previously input shape of the guide hole and the shape of the guide hole image, and then to correct the shape of the reflected target image based on this inclination.

The computing control circuit 51 and display apparatus 52 are housed separately from the body 10 which houses the measuring optical system 40.

The operation of the computing control circuit 51 will now be described.

With the quick return mirror 39 withdrawn from the observing and illuminating optical systems as shown by the dotted line, the halogen lamp 31 is switched on so that illuminating light from the lamp irradiates the subject's eye E through the illuminating optical system 30.

The operator, while observing through the eyepiece lens 26, roughly positions the indicator plate 60 with his hand between the objective lens 36 and the subject's eye E. An image of the target 62, which is a ring pattern on the indicator plate 60, is thereby projected by the illuminating light onto the cornea C of the subject's eye. The image of the target reflected by the cornea C is guided by the guide hole 61 and observing optical system 20 to the operator's eye S, and the operator positions the indicator plate 60 correctly based on this reflected target image.

The operator activates a switch (not shown) for taking measurements, interposes the quick return mirror 39 in the illumination path for making observations as shown by the solid line, and switches on the xenon lamp 37 to provide illumination for taking measurements. Illumination for taking measurements from the xenon lamp 37 then irradiates the subject's eye E through the indicator plate 60.

A reflected target image 62a is formed on the photodetector 43 via the measuring optical system 40 as shown in FIG. 4. Light reflected by the tapered surfaces 61a of the indicator hole 60 is also guided to the photodetector 43 via the measuring optical system 40, and the shape of the guide hole 61, i.e. an image 61b of the guide hole, is thereby projected onto the photodetector 43 as shown in FIG. 4.

The image information from this photodetector 43 is input to the computing control circuit 51 via the frame memory 50. This computing control circuit 51 is set to compute the inclination of the indicator plate 60 with respect to the measuring optic axis Z from the shape of the guide hole 61 previously input to a memory, not shown, and the shape of the image 61b of the guide hole. Based on this inclination, the circuit 51 performs a shape correction of the reflected target image 62a.

This correction by the computing control circuit 51 may be performed, for example, by means of the computational equations shown below. These computational equations will be described with reference to FIGS. 5 to 7.

Figures 5, 6:
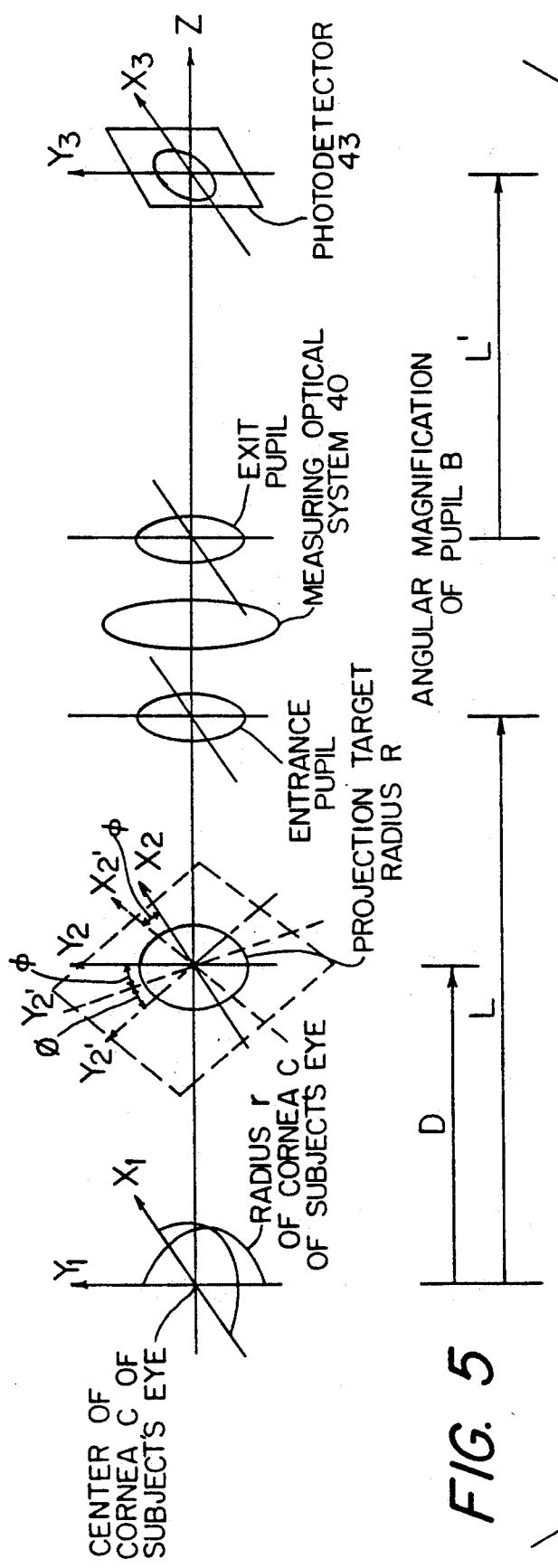
FIG. 5 is a schematic drawing used to describe the correction of the shape of the reflected target image.
FIG. 6 is a schematic drawing used to describe the correction of the shape of a corneal image.

The symbols shown in FIG. 5 have the following significance:

$O_1$ = center of curvature of cornea C of the subject's eye
r = radius of curvature of cornea C of subject's eye
D = distance from $O_1$ to center $O_2$ of indicator surface 60b of indicator plate 60
L = distance from $O_1$ to incidence pupil or entrance pupil $O_3$ of measuring optical system 40
L' = distance from emergence pupil or exit pupil $O_4$ of measuring optical system to photodetector 43
$X_1, Y_1$ = coordinate axes intersecting 90 degrees with Z axis (optic axis) at $O_1$
$X_2, Y_2$ = coordinate axes intersecting at 90 degrees with Z axis at center $O_2$ of indicator surface 60b $X_2'$ = inclination position of coordinate axis $X_2$ when indicator surface 60b is rotated about Z axis by an angle $\psi$ $Y_2'$ = inclination position of coordinate axis $Y_2$ when indicator surface 60b is rotated about $X_2$ axis by an angle $\theta$ $X_3, Y_3$ = coordinate axes intersecting at 90 degrees with Z axis at photodetector 43

$\psi$ = inclination angle between coordinate axes $X_2, X_2'$ $\theta$ = inclination angle between $X_2$—$Y_2$ plane and axis $Y_2'$ Q = optical center of incidence pupil or entrance pupil Q' = optical center of emergence pupil or exit pupil R = projection target radius B = angular magnification of pupil In FIG. 5, it is desirable that the indicator surface 60b on which the target to be projected is disposed, lies in the $X_2$—$Y_2$ plane, but this is difficult to realize in practice. Therefore, the computational equations used for the correction will now be described for the case in which the indicator surface 60b is rotated about the Z axis by an angle $\psi$, and about the $X_2'$ axis by an angle $\theta$. In other words, the computational equations described assume that the indicator surface 60b lies in a plane $X_2'$—$Y_2'$ in FIG. 5.

$$\begin{pmatrix} X_1 \\ Y_2 \\ Z_1 \end{pmatrix} = \begin{pmatrix} X_2 \\ Y_2 \\ Z_2 \end{pmatrix} + \begin{pmatrix} 0 \\ 0 \\ D \end{pmatrix}$$

$$\begin{pmatrix} X_2 \\ Y_2 \\ Z_2 \end{pmatrix} = A \begin{pmatrix} X_2' \\ Y_2' \\ Z_2' \end{pmatrix}$$

$$A = \begin{pmatrix} \cos\psi & -\sin\psi & 0 \\ \sin\psi & \cos\psi & 0 \\ 0 & 0 & 1 \end{pmatrix} \begin{pmatrix} 1 & 0 & 0 \\ 0 & \cos\theta & \sin\theta \\ 0 & -\sin\theta & \cos\theta \end{pmatrix} =$$

$$\begin{pmatrix} \cos\psi & -\sin\psi\cos\theta & -\sin\psi\sin\theta \\ \sin\psi & \cos\psi\cos\theta & \cos\psi\sin\theta \\ 0 & -\sin\theta & \cos\theta \end{pmatrix}$$

$$\therefore \begin{pmatrix} X_1 \\ Y_1 \\ Z_1 \end{pmatrix} = A \begin{pmatrix} X_2' \\ Y_2' \\ Z_2' \end{pmatrix} + \begin{pmatrix} 0 \\ 0 \\ D \end{pmatrix}$$

Therefore:

$$\text{and } A^{-1} = \begin{pmatrix} \cos\psi & \sin\psi & 0 \\ -\cos\theta\sin\theta & \cos\theta\cos\psi & -\sin\theta \\ -\sin\psi\cos\theta & \sin\theta\cos\psi & \cos\theta \end{pmatrix}$$

If the $X_2'$—$Y_2'$ plane is expressed in $X_1$—$Y_1$ coordinates, since $Z_2' = 0$:

$$-\sin\theta\sin\psi X_1 + \sin\theta\cos\psi Y_1 + \cos\theta(Z_1 - D) = 0 \quad (1)$$

The direct image will now be described with reference to FIG. 6.

Light emitted from a point $P_2(x_2', y_2')$ passes through the optic center of the incidence pupil (or entrance pupil) and the optic center of the emergence pupil (or exit pupil) so as to reach the photodetector 43. Considering this in reverse, if a point $P_3(x_3, y_3)$ on the photodetector 43 is measured, a point on the front of the subject's eye, i.e. $P_1(x_1, y_1)$ can be found from the following equations:

$$\left.\begin{array}{l} x_1 = -\dfrac{Lx_3}{L'B} \\ y_1 = -\dfrac{Ly_3}{L'B} \end{array}\right\} \quad (2)$$

A light ray which traverses P2 and Q passes through two points $(x_1, y_1, 0)$ and $(0, 0, L)$, and can therefore be described by the following equations:

$$\left.\begin{array}{l} X = K_1 x_1 \\ Y = K_1 y_1 \\ Z = -K_1 L + L \end{array}\right\} \quad (3)$$

The point of intersection of this direct ray (3) and the plane $X_2'$—$Y_2'$ is $P_2$. From equations (1) and (3), therefore, the point $P_2$ is:

$$\left.\begin{array}{l} x_2' = K_1' x_1 \\ y_2' = K_1' y_1 \\ Z_2' = -K_1' L + L \end{array}\right\} \quad (4)$$

where $$K_1' = \frac{(L-D)\cos\theta}{x_1\sin\theta\sin\psi - y_1\sin\theta\cos\psi + L\cos\theta}$$

As the projection target is spherical, the condition:

$$x_2'^2 + y_2'^2 = R^2 \quad (5)$$

must be satisfied.

From equation (4):

$$x_1^2 + y_1^2 = \left(\frac{R}{K_1'}\right)^2 \quad (6)$$

In equations (4) and (6), L', B and R are constants, and there are three unknowns: (D-L), $\theta$ and $\psi$.

If a measurement is taken of three points $(x_3, y_3)$, three equations will be obtained for three unknowns and so D-L, $\theta$, $\psi$ can be found.

Next, the reflected image from the cornea of the subject's eye will be described with reference to FIG. 7.

In FIG. 7, light emitted from the point $P_2$ is reflected at a point P (x,y,z) on the cornea C of the subject's eye, and passes through Q and Q' so as to reach the point $P_3$ $(x_3, y_3)$ on the photodetector 43. The line which passes through P and Q therefore has the same form as (2) and (3). Herein, the radius of curvature of the cornea C at the point P and in its vicinity is r, and the reflection angle at the cornea C of the subject's eye is $U_0$.

Therefore, the coordinates of P may be found from equations (7) and (8) as follow:

spherical condition: $X^2 + Y^2 + Z^2 = r^2$ \quad (7)

linearity condition:
$$\left.\begin{array}{l} X = K_2 x_1 \\ Y = K_2 y_1 \\ Z = -K_2 L + L \\ x_1 = -\dfrac{L x_3}{L'B} \\ y_1 = -\dfrac{L y_3}{L'B} \end{array}\right\} \quad (8)$$

The result is:

$$\left.\begin{array}{l} x = K_2' x_1 \\ y = K_2' y_1 \\ Z = -K_2' L + L \\ \text{where:} \\ K_2' = \dfrac{L^2 - \sqrt{L^2 r^2 - (L^2 - r^2)(x_1^2 + y_1^2)}}{x_1^2 + y_1^2 + L^2} \end{array}\right\} \quad (9)$$

Also, the line passing through the points O and P is as follows $$\left.\begin{array}{l} X = K_3 x \\ Y = K_3 y \\ Z = K_3 z \end{array}\right\} \quad (10)$$

The line passing through P and $P_2$ is then found, and the coordinates of P are found as the intersection of this line and the plane $X_2'$-$Y_2'$.

First, the line which passes through P and $P_2$ passes at least through the point P, so we may write:

$$\left.\begin{array}{l} X = K_4 + x \\ Y = K_4 b + y \\ Z = K_4 c + z \end{array}\right\} \quad (11)$$

The line given by equation (11) must also be in the plane generated by the lines represented by equations (8) and (10). As the plane generated by the lines (8) and (10) is the plane formed by the three points (0,0,0), (0,0,L), (x,y,z):

$$yX - xY = 0 \quad (12)$$

Substituting equation (12) in equation (11):

$$b = \dfrac{y}{x} \quad (13)$$

Equation (11) may therefore be written as follows:

$$\left.\begin{array}{l} X = K_4 + x \\ Y = K_4 \dfrac{y}{x} + y \\ Z = K_4 c + z \end{array}\right\} \quad (11)'$$

As the angle between the lines (8) and (10) is equal to the angle between the lines (10) and (11'):

$$\cos U0 = \dfrac{-x^2 - y^2 + Z(L - Z)}{\sqrt{x^2 + y^2 + z^2} \cdot \sqrt{x^2 + y^2 + z^2}} \quad (14)$$

$$\cos U0 = \dfrac{x + \dfrac{y^2}{x} + Zc}{\sqrt{x^2 + y^2 + z^2} \cdot \sqrt{1 + \left(\dfrac{y}{x}\right)^2 + c^2}}$$

From equations (14) and (9), C may be found as:

$$c = c\,(r;\ x_1,\ y_1,\ L) \quad (15)$$

The point of intersection between equation (11') and $X_2'$—$Y_2'$, from equations (11') and (1), is given by:

$$\left.\begin{array}{l} x_2' = K_4' + x \\ y_2' = K_4' \dfrac{y}{x} + y \\ z_2 = K_4' c + z \\ K_4' = -\dfrac{x^2 \sin\theta \sin\psi - xy\theta \cos\psi - x(Z - D)\cos\theta}{x^2 \sin\theta \sin\psi - y \sin\theta \cos\psi - xc\cos\theta} \end{array}\right\} \quad (16)$$

As the projection target is spherical:

$$x_2{}^- + y_2{}^- = R^{-2} \quad (17)$$

Therefore, substituting equation (16) in equation (17):

$$(x^2+y^2)K_4{}^{-2} + 2x(x^2+y^2)K_4{}^- + x^2(x^{-2}+y^2-R^{-2}) = 0 \quad (18)$$

Substituting equation (18) in equation (16), the function f(c) can be found.

From equation (15), C is a function of r. From equations (8) and (9), therefore:

$$g = (r;\ x_3,\ y_3,\ L,\ L^-,\ R^-,\ B,\ \theta,\ \psi) = 0 \quad (20)$$

As L, L', R', B, $\theta$, $\psi$ are known and $x_3, y_3$ can be found from measurement, r can therefore be found.

The power (refractive power) of the cornea of the subject's eye can be computed as follows. If angles are measured from $X_1$ and $Y_1$, the direction of the meridian may be considered as the angle which the plane represented by equation (12) makes with the plane $X_1 = 0$:

$$\begin{aligned} \phi &= \tan^{-1}\left(\dfrac{-x}{y}\right) \\ &= \tan^{-1}\left(-\dfrac{x_3}{y_3}\right) \end{aligned} \quad (21)$$

If the radius r of the cornea C is known, the refractive power of the cornea may be found from the relation:

$$Dpt = 1000 \cdot \dfrac{n - 1}{r} \quad (22)$$

where n is the refractive index of the cornea = approx. 1.336.

This calculation is performed successively for corneal reflected images $(x_3, y_3)$. If maxDpt, minDpt, $\psi$ max and $\psi$ min are found, astigmatism power, strong meridian, weak meridian and spherical power may be determined from:

$$\begin{aligned}\text{astigmatism power} \quad &\max Dpt - \min Dpt \\ \text{strong meridian} \quad &\phi\max \\ \text{weak meridian} \quad &\phi\min\end{aligned} \Bigg\} \quad (23)$$

spherical power   $\max Dpt$(taking the strong meridian as reference)

The maximum (maxDpt) and minimum (minDpt) of this spherical power may be found as follows.

If a target 62 having a radius R as shown in FIG. 8(b) is projected onto the cornea C of a subject's eye in FIGS. 1 and 2, a reflected target image 62a as shown in FIG. 8(a) is formed on the photodetector 43. The computing control circuit 51 then takes three convenient points $(x_3,y_3)$ on the corneal reflected image formed on the photodetector 43, i.e. $(x_{31},y_{31})$, $(x_{32},y_{32})$, $(x_{33},y_{33})$, and finds the respective distances $r_1, r_2, r_3$ from the optic axis to these points $(x_{31},y_{31})$, $(x_{32},y_{32})$, $(x_{33},y_{33})$.

Further, if the cornea of the subject's eye is assumed to be a toric surface, A, B and H can be found from the ellipse equation:

$$AX^2 + BY^2 + 2HXY = 1$$
$$X_k = r_k \sin\phi_k$$
$$Y_k = r_k \cos\phi_k$$
$$(k = 1, 2, 3)$$

$$\tan 2\phi\max = \frac{-2H}{A - B}$$

$$\frac{1}{r^2\max} = \frac{B\sin^2\phi\max - a\cos^2\phi\max}{\sin^2\phi - \cos^2\phi}$$

$$\frac{1}{r^2\min} = \frac{A\sin^2\phi\max - B\cos^2\phi\max}{\sin^2\phi\max - \cos^2\phi\max}$$

The maximum (maxDpt) and minimum (minDpt) of the spherical power are then given as:

$$\max Dpt = 1000 \cdot \frac{n-1}{r\min}$$

$$\min Dpt = 1000 \cdot \frac{n-1}{r\max}$$

Alternatively, more than three measurement points can be taken, and the ellipse coefficients A, B and H determined approximately by the method of least squares.

In the aforesaid embodiment, the transparent indicator plate 60 was used as an indicator. The invention is not, however, limited to this arrangement, and a kerato ring 70 of the type shown in FIG. 10, for example, may also be used as the indicator.

In FIG. 10, the kerato ring 70 is formed from an inverted metal cone, and includes an envelope 71 having an inverted conical inner surface. Inside this envelope 71, annular reflecting surfaces 72 extending in a circumferential direction are formed concentrically in a stepwise manner, and annular target reflecting surfaces 73 extending in a circumferential direction but vertically inclined are also formed concentrically. The reflecting surfaces 72 are scattering reflecting surfaces provided with fine imperfections, and the target reflection surfaces 73 are formed as mirrors. In the FIG. 70a is a guide hole in the envelope 70.

The kerato ring 70 is interposed between the pupil E of the subject's eye and an objective lens 35. If the kerato ring 70 were not inclined, part of the illuminating light from the halogen lamp 31 would be reflected at the multiple reflecting surfaces 72, and be observed by the operator S via the observing optical system 20 as concentric rings. The remainder of the illuminating light from the halogen lamp 31 would be reflected by the target reflecting surfaces 73, and projected onto the cornea C of the subject's eye where it would be reflected. If the kerato ring 70 were not inclined and the cornea was not deformed, the reflected light from the cornea C would then be observed via the observing optical system as concentric rings.

It can be confirmed by visual observation that if the images of the multiple concentric reflecting surfaces 72 appear to be similar, the kerato ring is not inclined and is arranged substantially in the correct position.

It is, however, difficult to position the kerato ring correctly. An arrangement is therefore chosen in which corrections are automatically applied so that accurate measurements can be made even if the kerato ring has a slight inclination.

For this purpose, shape data concerning the reflecting surfaces 72 are first entered in a memory, not shown. The computing control circuit 51 then computes the inclination of the kerato ring 70 based on the image signal at the photodetector 43 from the reflecting surfaces 72 and the shape of the reflecting surfaces 72.

Even if the kerato ring 70 is inclined, therefore, the computing control circuit 51 corrects the reflected target image from the subject's eye E from the inclination of the kerato ring 70.

As described hereintofore, the apparatus of this invention corrects errors due to the inclination of the optic axis of an indicator with respect to the optic axis of the measuring optical system when a hand-held indicator is used. Therefore, even if the optic axis of the indicator is inclined with respect to the optic axis of the measuring optical system during measurements, the shape of the cornea of a subject's eye can be accurately determined from the image of a target indicator reflected by the cornea.

What is claimed is:

1. A corneal shape measuring apparatus comprising:
an illuminating optical system for illuminating a cornea of a subject's eye;
a measuring optical system having an objective lens on which light reflected by the cornea of the subject's eye illuminated by said illuminating optical system impinges;
an indicator having a visual target projected onto said cornea by said illuminating light, said indicator being disposed between said objective lens and the subject's eye;
a light guide hole for guiding an image of the target reflected by said cornea to said objective lens;
reflecting surfaces aligned with said guide hole, for reflecting an image of said guide hole to said objective lens;
a photodetector on which said reflected target image is projected and on which the guide hole image from said reflecting surfaces is projected by reflected light;
computing circuit means for calculating a shape of said reflected target image based on a corresponding signal from said photodetector, computing an inclination of the indicator with respect to a measuring axis from the shape of said guide hole previously inputted and the shape of said guide hole image, and correcting the shape of said reflected target image accordingly based on the computed inclination to determine a deformation of the cornea of the subject's eye; and display means for displaying the shape of the subject's eye obtained by said computing circuit means.

2. A corneal shape measuring apparatus according to claim 1, wherein said computing circuit means and display means are housed separately from a body housing the measuring optical system.

3. A corneal shape measuring apparatus according to claim 1, wherein said indicator is a transparent plate and said visual target is a ring pattern on said plate concentric with said guide hole and said reflecting surfaces.

4. A corneal shape measuring apparatus according to claim 3, wherein said ring pattern comprises multiple rings of different diameters.

5. A corneal shape measuring apparatus according to claims 3 or 4, wherein said ring pattern is provided on a surface adjacent to the cornea of a subject's eye.

6. A corneal shape measuring apparatus according to claim 3, wherein said visual target comprises tapered reflecting surfaces oriented towards said objective lens and aligned with said guide hole.

7. A corneal shape measuring apparatus according to claim 1, wherein said reflecting surfaces are formed concentrically with said guide hole in said indicator.

8. A corneal shape measuring apparatus according to claim 1, wherein said reflecting surfaces are annular reflecting surfaces extending in a circumferential direction and formed in a stepwise manner on an inner surface of an inverted cone, and said indicator further includes target reflecting surfaces extending in a circumferential direction for reflecting illuminating light towards the cornea of the subject's eye.

9. A corneal shape measuring apparatus according to claim 1, wherein said reflecting surfaces are scattering and reflecting surfaces.

* * * * *